United States Patent
Pagani et al.

(10) Patent No.: US 9,791,303 B2
(45) Date of Patent: Oct. 17, 2017

(54) PACKAGE, MADE OF BUILDING MATERIAL, FOR A PARAMETER MONITORING DEVICE, WITHIN A SOLID STRUCTURE, AND RELATIVE DEVICE

(71) Applicant: STMICROELECTRONICS S.r.l., Agrate Brianza (IT)

(72) Inventors: Alberto Pagani, Nova Milanese (IT); Bruno Murari, Monza (IT); Federico Giovanni Ziglioli, Pozzo d'adda (IT); Marco Ronchi, Monza (IT); Giulio Ricotti, Broni (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 214 days.

(21) Appl. No.: 14/401,332

(22) PCT Filed: May 23, 2013

(86) PCT No.: PCT/EP2013/060669
§ 371 (c)(1),
(2) Date: Nov. 14, 2014

(87) PCT Pub. No.: WO2013/174946
PCT Pub. Date: Nov. 28, 2013

(65) Prior Publication Data
US 2015/0135846 A1    May 21, 2015

(30) Foreign Application Priority Data
May 25, 2012 (IT) .............................. MI2012A0912

(51) Int. Cl.
*G01D 11/24* (2006.01)
*G01M 5/00* (2006.01)
(Continued)

(52) U.S. Cl.
CPC ........ *G01D 11/245* (2013.01); *B28B 23/0031* (2013.01); *G01K 17/00* (2013.01);
(Continued)

(58) Field of Classification Search
CPC ................................ G01N 33/383; G01L 1/18
See application file for complete search history.

(56) References Cited

U.S. PATENT DOCUMENTS 4,590,505 A *  5/1986  Bluzer .............. H01L 27/14831
                                                  257/225
6,405,592 B1   6/2002  Murari et al.
(Continued)

FOREIGN PATENT DOCUMENTS

CN          101216412        7/2008
WO         2004068095        8/2004

OTHER PUBLICATIONS

Fuat Koksal, Fatih Altun, Ilhami Tigit, Yusa Sahin; "Combined effect of silica fume and steel fiber on the mechanical properties of high strength concretes" Journal of Contsruction and Building Materials, Published online Jun. 15, 2007.*
(Continued)

*Primary Examiner* — R. A. Smith
*Assistant Examiner* — John M Royston
(74) *Attorney, Agent, or Firm* — Slater Matsil, LLP

(57) ABSTRACT

A package for a device to be inserted into a solid structure may include a building material that includes particles of one of micrometric and sub-micrometric dimensions. The device may include an integrated detection module having at least one integrated sensor and the package arranged to coat at least one portion of the device including the integrated detection module. A method aspect includes a method of manufacturing the device. A system aspect is for monitoring parameters in a solid structure that includes the device.

37 Claims, 11 Drawing Sheets

(51) Int. Cl.
*B28B 23/00* (2006.01)
*G01K 17/00* (2006.01)
*G01L 1/18* (2006.01)
*G01N 33/38* (2006.01)

(52) U.S. Cl.
CPC .............. *G01L 1/18* (2013.01); *G01M 5/00* (2013.01); *G01N 33/383* (2013.01)

(56) References Cited

U.S. PATENT DOCUMENTS

| | | |
|---|---|---|
| 6,480,699 B1 | 11/2002 | Lovoi |
| 6,950,767 B2 | 9/2005 | Yamashita et al. |
| 7,987,728 B2 | 8/2011 | Song et al. |
| 2002/0154029 A1 | 10/2002 | Watters et al. |
| 2005/0061076 A1 | 3/2005 | Kim |
| 2005/0241403 A1 | 11/2005 | Thomson et al. |
| 2007/0018083 A1 | 1/2007 | Kumar et al. |
| 2007/0228500 A1* | 10/2007 | Shimazu ............... G01B 7/18 257/417 |
| 2008/0034884 A1 | 2/2008 | Song et al. |
| 2009/0033467 A1* | 2/2009 | Finocchiaro ............. H04B 5/00 340/10.1 |
| 2010/0148926 A1* | 6/2010 | Kang ............... G06K 19/07767 340/10.1 |
| 2010/0238027 A1* | 9/2010 | Bastianini ............. G01D 9/005 340/540 |
| 2011/0011224 A1* | 1/2011 | Levene ................... B26D 5/34 83/13 |
| 2011/0021887 A1* | 1/2011 | Crivelli ................ G01D 11/245 600/302 |
| 2011/0221014 A1* | 9/2011 | Nakatani ............ B81C 1/00158 257/417 |
| 2012/0068827 A1 | 3/2012 | Yi et al. |

OTHER PUBLICATIONS

Barlian et al., "Semiconductor Piezoresistance for Microsystems", Proceedings of the IEEE, vol. 97, No. 3, Mar. 2009, pp. 513-552.

* cited by examiner

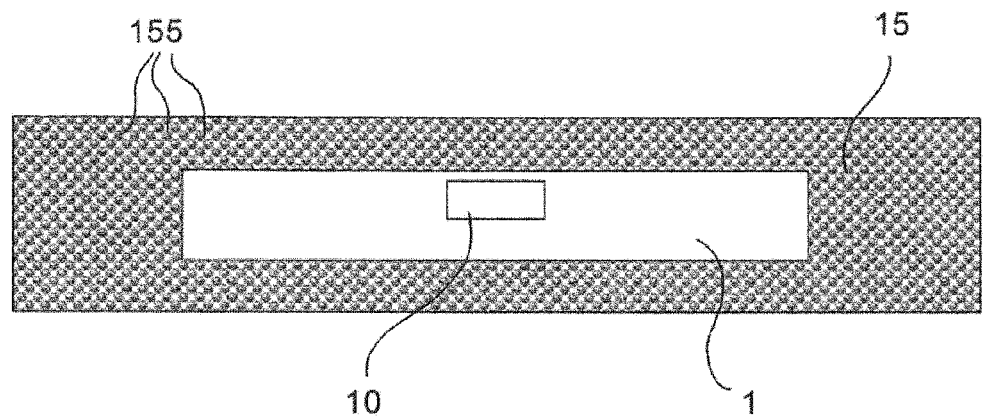
FIG. 1
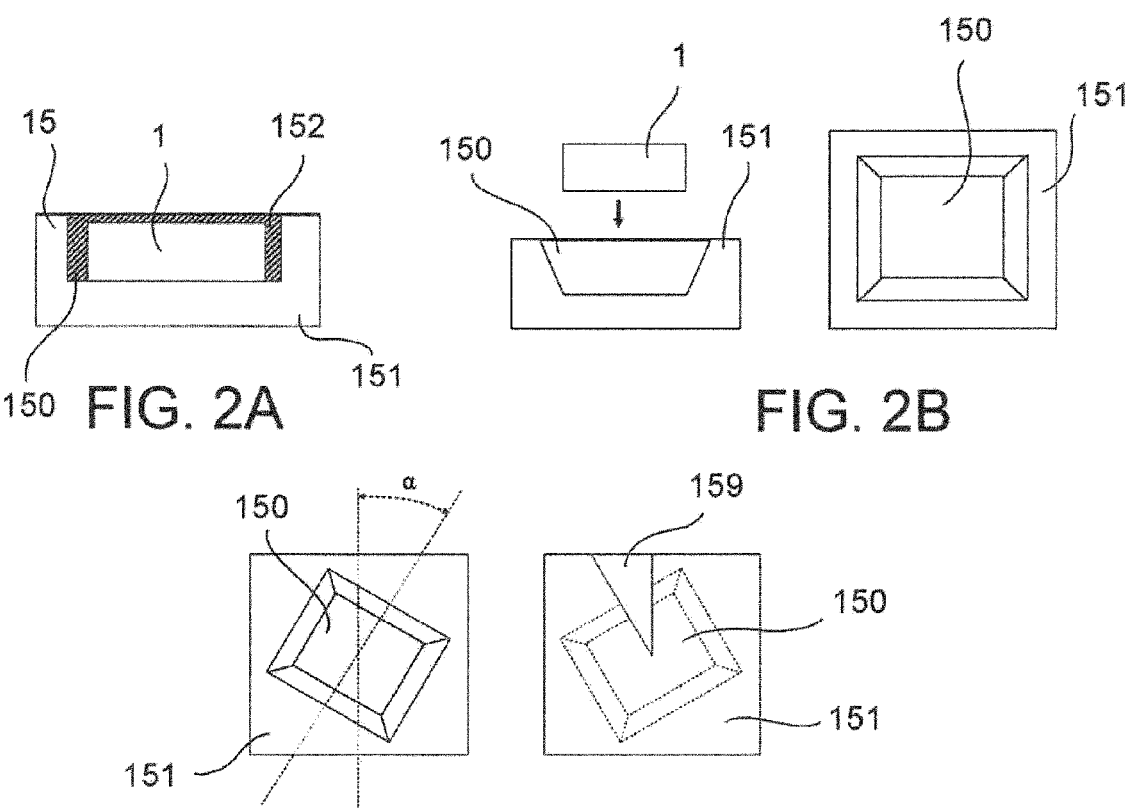
FIG. 2A
FIG. 2B
FIG. 2C

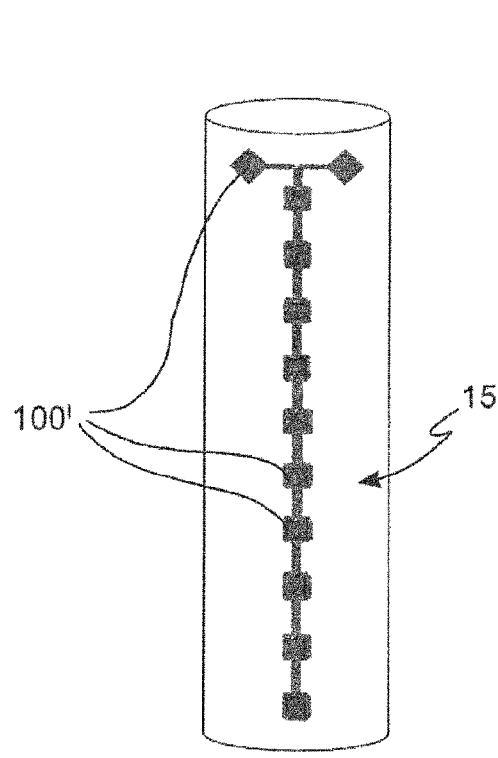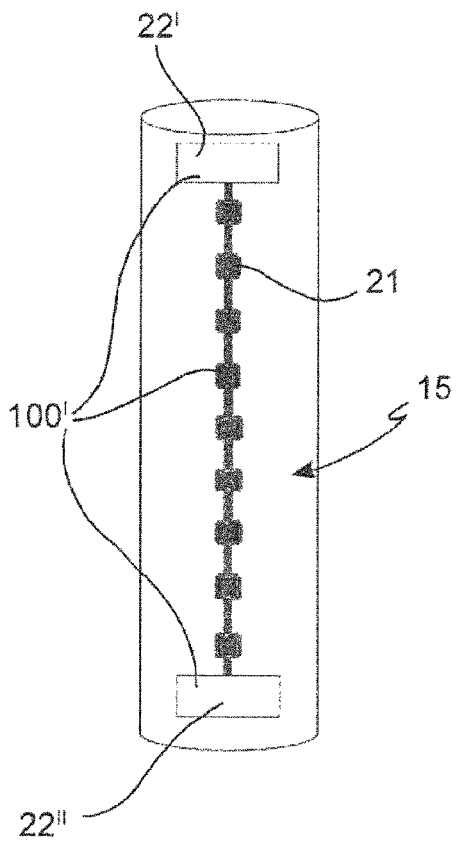
FIG. 14A    FIG. 14B
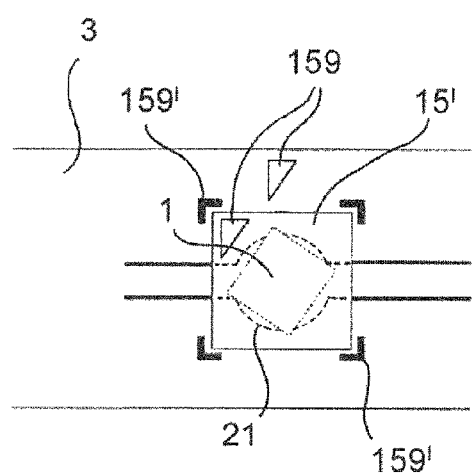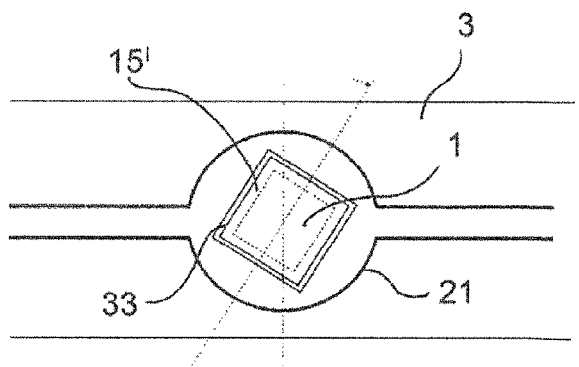
FIG. 15A    FIG. 15B

PACKAGE, MADE OF BUILDING MATERIAL, FOR A PARAMETER MONITORING DEVICE, WITHIN A SOLID STRUCTURE, AND RELATIVE DEVICE

FIELD OF THE INVENTION

The present invention relates to integrated electronic devices for monitoring parameters within a solid structure, and, in particular to packages for such devices, having characteristics that are specific for such type of application.

BACKGROUND OF THE INVENTION

In solid structures, particularly in load-bearing structures of, for example, bridges, buildings, tunnels, railways, containment walls, dams, embankments, slabs and beams of buildings, pipelines and underground structures of city underground railways, and so on, it may be particularly helpful to monitor significant parameters, such as, for example, pressure, temperature, and mechanical stresses. Such monitoring, carried out periodically or continuously, may be useful both in the initial step and during the life time of the structure.

To this aim, it is known to use electronic monitoring devices based on electronic sensors, which are capable of providing relatively good performance at relatively low costs. Usually, such devices are applied on the surface of the structures to be monitored, or within recesses already provided in the structure and accessible from the outside.

However, such devices are not generally capable of exhaustively detecting the parameters within the structure to be monitored, which may be very useful for assessing the quality of the structure, the safety thereof, its aging, the reaction to variable atmospheric conditions, etc. Furthermore, such devices can typically only be applied after the structure has been built, and not while it is being built. Therefore, these devices are unable to evaluate possible initial defects.

As a partial response to these desires, the approach shown in the U.S. Pat. No. 6,950,767, provides an electronic monitoring device that is entirely contained, i.e., "buried" within the material (for example, reinforced concrete) of the structure to be monitored. Such a device is a whole system encapsulated in a single container, including several parts that are assembled on a substrate, such as integrated circuits, sensors, antennas, capacitors, batteries, memories, control units, and still other substrates, formed in different "chips" that are mutually connected by electrical connections, for example, metal connections.

Therefore, on the whole, U.S. Pat. No. 6,950,767 discloses an approach using a "System in Package" (SiP) in which the SiP is coated in a casing of mold material, such as an epoxy resin. The casing may be a conventional package, per se known. Such a system communicates with the exterior by virtue of a radio communication subsystem included therein, having antennas of dimensions suitable to communicate with a remote system.

It is noted that a device or a monitoring system operating within a solid structure may desirably address particular operative conditions. For the present description, solid structures are considered, such as structures made of building material, for example cement, concrete, mortar.

A monitoring device or system to be initially "buried" in a building material (e.g., uncured concrete, which then cures and solidifies) and to remain then "buried" in the solid structure, is subjected to important operative conditions.

Furthermore, it is in contact with a material having irregularities, from several points of view, due to intrinsic characteristics or imperfections. All of this causes at least two types of drawbacks, respectively correlated to reliability problems and to possible measurement inaccuracies, which are described below. Referring to reliability problems, considerable causes for wear are, for example, relatively high pressures, also of some hundreds of atmospheres, as well as causes related to water seepage, over time, which may damage the system.

A drawback of the known systems, such as the one described in U.S. Pat. No. 6,950,767 is that they are relatively complex systems and may be damaged due to the operative conditions in which they have to operate. In particular, the electric interconnections between the various components of the SiP described in U.S. Pat. No. 6,950,767 can be vulnerable due to the mechanical stress subjected to the SiP inserted in the structure.

Furthermore, the "window" that has to be left in the package to allow the sensor to detect the corresponding parameter may be a weak point due to possible moisture seepage. Again, a crack or imperfection of the coating material may let water penetrate within the SiP, causing short-circuits. Besides water, other substances, such as potentially corrosive acids, can penetrate.

In general, although they are designed for such use, the reliability of systems such as the one described in U.S. Pat. No. 6,950,767 has its limit in the complexity of the structure of such a system, although miniaturized, and the unsuitability of the commonly used known types of packages, due to extreme conditions.

Referring to problems of incorrect or inaccurate measurement, initially, it may be considered that the solid structure to be monitored includes a material that may not be perfectly homogeneous. For example, concrete is an artificial stone material formed of stone aggregates having different dimensions, referred to also as inert, which are bonded with cement, as a hydraulic binder activated by a chemical reaction with water. Therefore, in concrete it may be possible to classify cement granules (having a dimension ranging from 1 to 50 µm) and a wide variety of granules of inert aggregates, which, quantitatively, can account for up to 80% of the weight. The concrete inert aggregates are usually classified, based upon the diameter of the granules thereof, such as very fine, or fillers (diameter<0.063 mm); fine, or sand/grit (0.063-4 mm); coarse fine gravel/finely crushed stone, (4-15 mm); and gravel/crushed stone, (15-40 mm).

As it may be known in the field of building construction, that different types of concrete can be obtained with mixtures composed of inert aggregates of different dimensions in various percentages. Such different types of concrete have different characteristics, in terms of properties such as mechanical resistance, porosity, compactness, and lightness. In any case, to obtain a concrete that may meet minimum requirements for each of the above-mentioned properties, it may be desirable to use a mixture of inert aggregates having different granularities.

With respect to very fine inerts, microsilica or silica fume is sometimes used, which may include particles having a diameter ranging between 0.01 and 1 µm. Microsilica behaves as a very fine filler, suitable to fill the free spaces between the cement granules, thus increasing the cement compactness. On the other hand, due to the high specific surface of the microsilica particles, they cannot typically be used in percentages above 10%, which may excessively increase the slurry water amount. In other types of concrete, the fine and very fine aggregates may be present in a minimum percentage.

Therefore, it shall be noted that, at a millimetric or sub-millimetric scale, the concrete intrinsically has, due to its nature, irregularities that are randomly distributed within the volume of the solid structure it forms. In addition, there may be local imperfections.

In such conditions, a monitoring device may be considered, for example, arranged in a specific position of a concrete structure, suitable to detect a force (for example, corresponding to a mechanical stress) applied by the solid structure, at a macroscopic level, in that specific position, and along a certain direction, for example, a vertical direction. The device locally detects the force in the point of the surface of an integrated circuit, included therein, in which there is a sensor.

Such a sensor is typically sensitive to the piezoresistive effect, and it is capable of measuring a force in a determined direction, which is made to match, in the initial positioning step, to the direction of interest (for example, a vertical one). If the force, while keeping the intensity constant, is applied to a different direction, the sensor sensitivity decreases, in accordance with the piezoresistive effect, and the actually detected force turns out to be lower, sometimes significantly lower.

On the other hand, due to the above-mentioned characteristics of the concrete, the sensor buried in the solid structure may be in contact with a part of the structure locally having very different and inhomogeneous characteristics (presence or absence of micro-cavities, presence or absence of coarse particles, or co-presence of particles having different dimensions, etc.) Such particles may exert a punctual action on a microscopic scale, which may be different from the macroscopic action to be correctly detected.

In particular, it may be possible that the concrete locally exerts a force upon the sensor through particles having a variable granularity in a different direction than the macroscopic direction of the force that is to be detected. Consequently, the sensor, due to the characteristics thereof, illustrated above, detects a force intensity that is lower than the actual one.

The described example shows how, by using known devices, particularly severe measurement errors may be originated, even systematic errors. In brief, if a general known monitoring device is buried within a solid structure, with an integrated circuit without a package, inaccuracy problems may arise (or even systematic errors) during the measurements.

If a general known monitoring device is buried within a solid structure, having a package of a common type, relatively severe reliability problems may arise, i.e., high probabilities of damage over time. Also in this case, further measurement errors may originate. For example, the conventional packages can be subjected to a volume reduction following a degassing phenomena that may alter, for example, pressure measurements. Furthermore, the interface between the package material and the solid structure material may not allow such an adhesion to correctly transmit a parameter to be measured.

SUMMARY OF THE INVENTION

Thus, the present embodiments provide a package for an integrated electronic device to be used to monitor parameters within a solid structure, as well as the monitoring device itself, which are improved to at least partially obviate the drawbacks described herein above with reference to the prior art. In particular, a package and a related device are disclosed, which are relatively simple and have an enhanced robustness and wear resistance while allowing measurements that are more accurate compared to those allowed by the known packages and devices.

In particular, a package for a device to be incorporated in a solid structure for the detection and monitoring of one or more local parameters is defined, in which such a package is made of a building material formed of particles having micrometric or sub-micrometric dimensions. Furthermore, a device for the detection and monitoring of one or more local parameters within a solid structure is defined. The device includes an integrated detection module having at least one integrated sensor, and a package arranged to coat at least one portion of the device including the integrated detection module. The package is made of a building material formed of particles of micrometric or sub-micrometric dimensions.

BRIEF DESCRIPTION OF THE DRAWINGS

FIG. 1 is a sectional view of a package made of building material and of a part of an electronic monitoring device according to an embodiment of the present invention.

FIGS. 2A, 2B, and 2C are diagrams of a package made of building material according to respective embodiments of the claimed invention.

FIGS. 11-13, 14A, 14B, 15A, and 15B are diagrams of monitoring devices according to respective embodiments of the claimed invention.

DETAILED DESCRIPTION OF THE EMBODIMENTS

Figure 3:
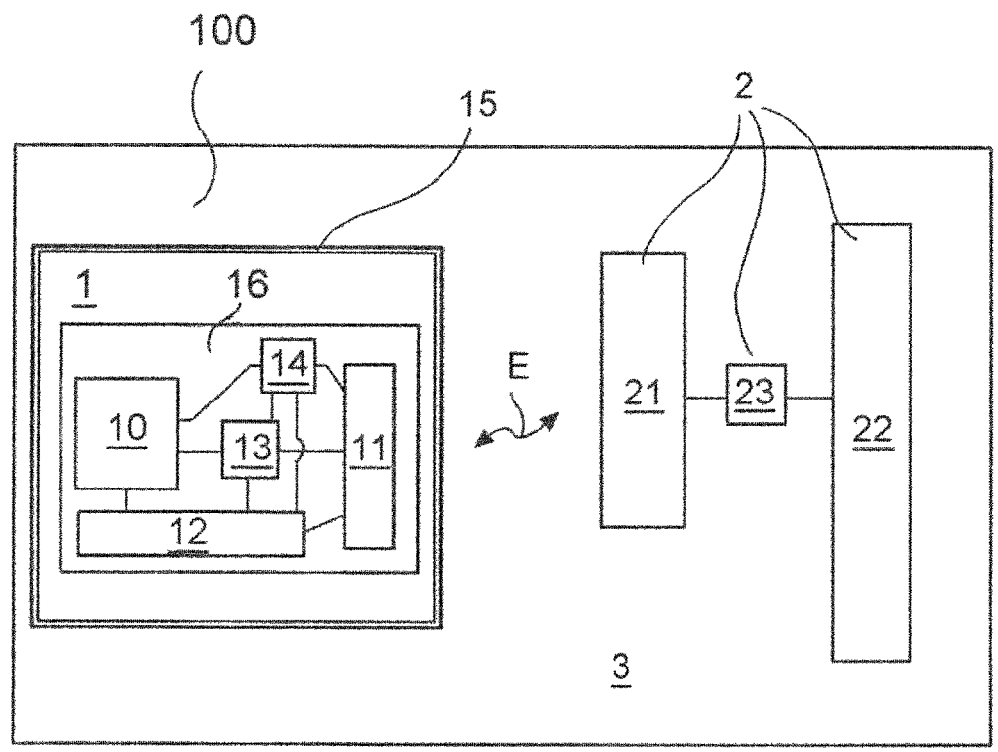
FIG. 3 is an operational block diagram of an electronic monitoring device according to an embodiment of the claimed invention.

With reference to FIG. 1, a package 15 for a device suitable to be incorporated in a solid structure for detecting and monitoring one or more local parameters is now described. The device, which will be described in more detail herein below, includes, besides the package 15, at least one integrated detection module 1 having an integrated sensor 10. Preferably, the integrated detection module 1 is formed on a single semiconductor chip (herein below, referred to simply as a chip) that is typically silicon-based.

The package 15 is manufactured with a building material formed of particles of micrometric or sub-micrometric dimensions. Such particles are indicated with the reference number 155 in the enlarged sectional view of FIG. 1.

Particles of micrometric dimensions may include particles having a diameter ranging between 1 μm (μm=micron, or micrometer) and some tens of μm, and particle of sub-micrometric particles may include particles having a diameter equal to or less than 1 μm. Preferably, the package 15 is formed of particles having a diameter less than 10 μm. More preferably, the package 15 is formed of particles having a diameter less than 1 μm.

In accordance with a embodiment, the package 15 is substantially isotropic on a millimetric scale, i.e., a scale from hundreds of μm to one millimeter and more. In such a case, the package 15 is formed exclusively (within the limits of the purity that can be obtained) from such particles of micrometric or sub-micrometric dimensions. Furthermore, such particles are distributed in a substantially homogeneous manner to obtain the above-mentioned isotropic property, at least on scales that are larger than the micrometric scale, and thus on a millimetric scale.

According to an embodiment, the particles of micrometric or sub-micrometric dimensions forming the package 15 are microsilica or silica fume particles, having dimensions ranging, for example, between 0.01 and 1 μm.

In particular, according to an embodiment, the package 15 is made of a building material formed of particles of micrometric or sub-micrometric dimensions 155, wherein such particles of micrometric or sub-micrometric dimensions 155 include microsilica or silica fume particles, so that the package 15 is isotropic and homogeneous on a millimetric scale.

In accordance with a particular embodiment, the package 15 is made of a building material formed from particles of cement and particles of microsilica or silica fume particles.

Advantageously, due to reasons that will be illustrated below, the particles of micrometric or sub-micrometric dimensions can also optionally include magnetic particles.

An embodiment of the package 15, shown in FIG. 2A, includes a housing portion 151 having a housing 150 for the integrated detection module 1, and a filling portion 152 shaped to entirely coat the integrated detection module 1. The housing 150 defines, for example, a parallelepiped-shaped or rectangularly-shaped recess. In a further implementation example illustrated in FIG. 2B, the housing 150 has a recess having a shape that guides and facilitates the proper positioning of the integrated detection module 1 within the same recess, for example, the shape of a frustum of a pyramid.

According to a further implementation example, shown in FIG. 2C, the housing 150 is rotated by a known angle α relative to an axes system of the package 15 to determine a predefined positioning of the integrated detection module 1 to detect at least one local parameter (for example, pressure) along a corresponding predefined direction related to the mentioned predefined positioning. In such a case, advantageously, a marker 159 is arranged, for example, on the rear part of the package, to indicate such angle, thereby allowing the proper positioning of the integrated detection module 1 within the building structure.

An electronic device 100 for detecting and monitoring one or more local parameters (hereinafter referred to also as a "monitoring device") within a solid structure, according to an example embodiment is now described. For this description, reference will be made in particular to FIGS. 3 and 4, related to functional and structural aspects of the device 100, respectively.

The monitoring device 100 includes an integrated detection module 1 having at least one integrated sensor 10, and a package 15 arranged to coat at least one portion of the device 100 including the integrated detection module.

As noted before, the integrated detection module 1 is preferably made on a single silicon chip. Therefore, the package 15 fully coats the chip by which the integrated detection module 1 is formed (FIG. 4 shows a sectional view of such full coating).

The package 15 is a package having any one of the combinations of characteristics already described above. In particular, such a package 15 may be manufactured with a building material formed of particles of micrometric or sub-micrometric dimensions. Furthermore, the package 15 may preferably be substantially isotropic on a millimetric scale.

Figure 4:
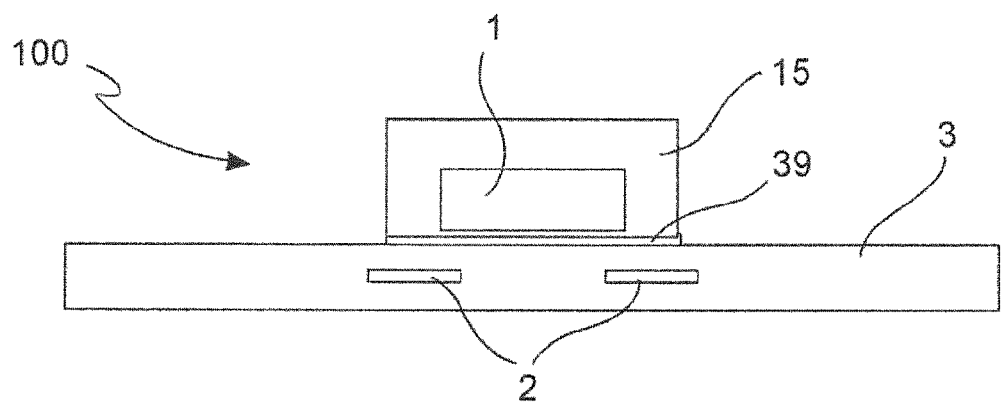
FIG. 4 is a sectional view of an electronic monitoring device according to an embodiment of the claimed invention.

The monitoring device 100 further includes electromagnetic means 2 or circuitry for transmitting/receiving electromagnetic signals and energy between the integrated detection module 1 and an external data collection and control system (per se known, not shown in FIGS. 3 and 4).

The monitoring device 100 further comprises support means 3, or device substrate configured to provide a support to the integrated detection module 1 and the electromagnetic means 2 or circuitry, making them mutually integral, and further configured to fix the device 100 to a supporting structure 211 (which will be illustrated in FIG. 16) passing through the points to be monitored within the solid structure. Therefore, the support means 3 may allow the monitoring device 100 to be maintained in a predefined position within the structure to be monitored. The support means 3 are formed by an advantageously flexible support, for example, made of a polymeric material, on which both the package 15 including the integrated detection module 1 (for example, by a gluing layer 39) and the electromagnetic means 2 are located.

With reference again to FIG. 3, it is noted that the detection module 1 includes, in particular, as noted before, an integrated sensor 10 capable of detecting and monitoring one or more parameters to be controlled, which are characteristic of the structure to be monitored. Typically, such parameters are a pressure and/or a temperature, and/or a mechanical stress. Moreover, it is noted that the detectable parameters may be different from those mentioned above, provided that they have a detectable effect on the semiconductor or on structures integrated in the single chip of the integrated detection module 1.

According to various embodiments, the sensors integrated in the integrated detection module 1 can be more than one, and each of them can detect one or more parameters. The integrated sensor 10 is capable of converting a temperature or pressure value into an electrical variable, for example, by exploiting the known variations induced by such parameters, for example, on the mobility of electrons/electron holes in the semiconductor.

In this regard, it may be known that the mobility depends on temperature in a manner that is independent from the crystal orientation of the semiconductor material, and on pressure (or on the force applied) in a manner that is dependent on the crystal orientation of the semiconductor material, according to the piezoresistive phenomenon. In particular, with reference to the Miller indices, by using common notations defining planes and axes characterizing a crystal, consider, for example, a crystal of the N type in the plane (001). In such example, the sensitivity to mechanical stress, i.e., the sensitivity to pressure, may be at a maximum if such stress is applied along the axes [100] and [010] with respect to a reference system associated to the crystal orientation, while it may be a minimum along the axes [110].

Therefore, by suitable configurations of the components integrated on the chip of the integrated detection module 1, it may be possible to build pressure sensors by compensating for the dependence on the temperature, or, vice versa, temperature sensors, by compensating for the dependence on the pressure. Other dependences on ageing and wear are distinguished from the above-mentioned ones, and are compensated for, taking into account that they emerge over much longer time periods, for example, years.

According to an implementation example, the sensor 10 is a pressure sensor formed with four resistors integrated in a Wheatstone bridge configuration. Two pressure-sensitive resistors are oriented along the axes [100] and [010] associated to the crystal orientation, while the other two are oriented along the axes [110], which orientation matches with the angle of the axis of minimum sensitivity of the piezoresistive effect. In this way, the dependence of the measurement on the "temperature" parameter is negligible, and in this sense, it may be possible to say that the "pressure" parameter is measured in a substantially independent manner from the "temperature" parameter.

According to a further implementation example, the sensor 10 is a pressure and temperature sensor made by a first and a second ring oscillator, each including a plurality of integrated components (for example, three or an odd number of inverters) in a cascade configuration. The integrated components of the first oscillator include a semiconductor material with a different crystal orientation from the orientation of the material of the second oscillator, for example, respectively, with an orientation along the axis [110] and [100] or [010].

In this way, the oscillation frequency of the first oscillator with an orientation at [110], and in which the piezoresistive effect may be a minimum, substantially depends only on the temperature. The pressure effect may be completely negligible. Therefore, such frequency can be seen as the output of a temperature sensor.

The oscillation frequency of the second oscillator with an orientation [100] or [010], if the temperature effect is subtracted and which effect is known by virtue of the output of the first oscillator, may substantially depend only on the pressure. Therefore, such frequency can be seen as the output of a pressure sensor. In the examples described above, the presence of membranes or components other than the integrated detection module 1 may not be necessary for the operation of the sensor 10.

Figure 5A:
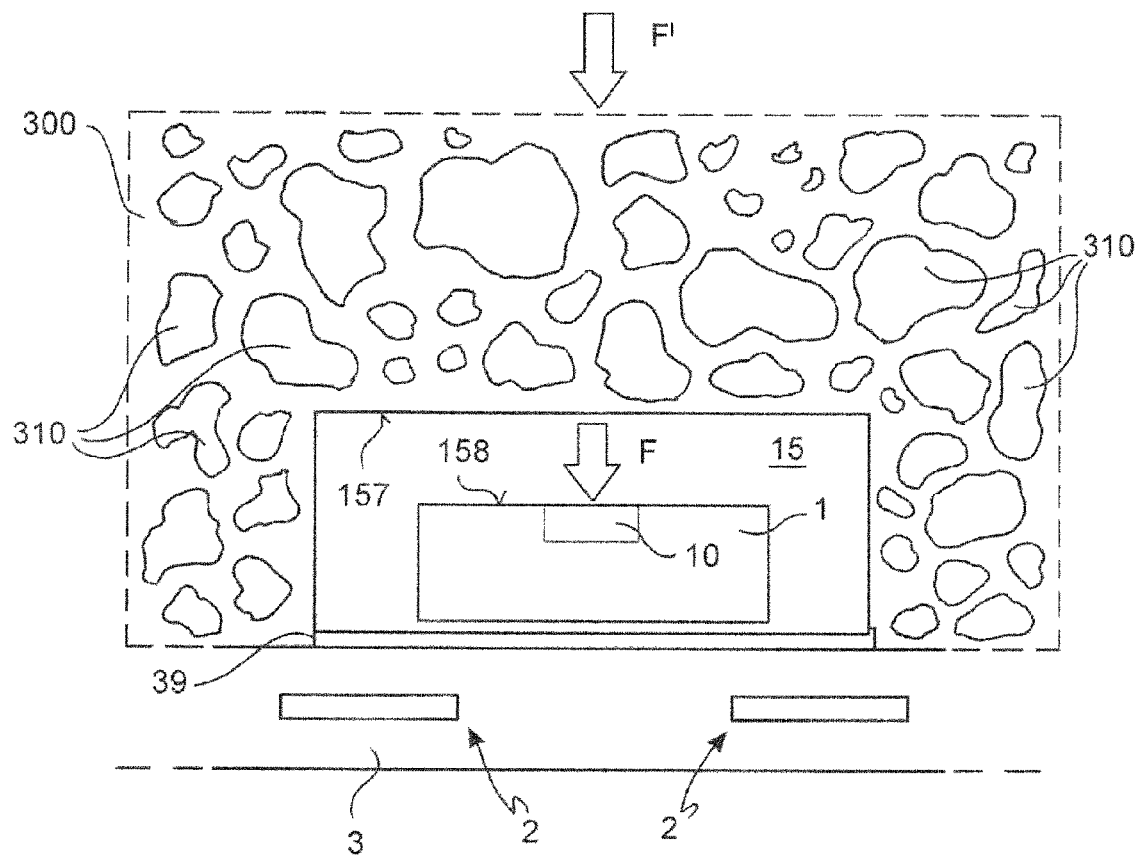
FIG. 5A is a more detailed view of the electronic monitoring device of FIG. 4.

Referring now to FIG. 5A, it is noted that in the device 100, the package 15 is arranged with an internal surface thereof 158 in contact with the integrated sensor 10, and with an external surface thereof 157 in contact with a portion of the solid structure 300 (in the illustrated example, concrete including granular particles 310). In this way, the package 15 separates the integrated sensor 10 from the solid structure 300, and, at the same time, allows a transfer to such integrated sensor 10, of one or more detectable quantities related to a corresponding local parameter and measured in the solid structure portion 300 in contact with the package 15.

Thus, on one hand, the package 15 is subjected to the action of the solid structure surrounding it (for example, of the part of structure above it). On the other hand, it may be capable of transmitting such an action, by contact, to the integrated sensor 10.

It may be considered, for example, the case where, within a concrete structure, a pressure proportional to the intensity of a force applied in a normal direction, for example, a vertical direction, with respect to the integrated detection module (force and direction are indicated by an arrow F' in FIG. 5A) has to be measured. Taking into account the irregularities and/or non-homogeneities of the structure to be monitored (for example, concrete), it may be possible that the force exerted by the structure, on a macroscopic scale and in the above-mentioned normal direction, is instead applied locally on a microscopic scale and along a different direction. In other words, the infinitesimal force contributions generated in the examined position by the different infinitesimal concrete regions, having a different consistency and direction in the various points (depending on the local presence of more or less coarse particles 310, or filler, or micro-cavities, etc.) can be combined to determine a force acting locally in a direction that is different from the normal one.

Figure 5B:
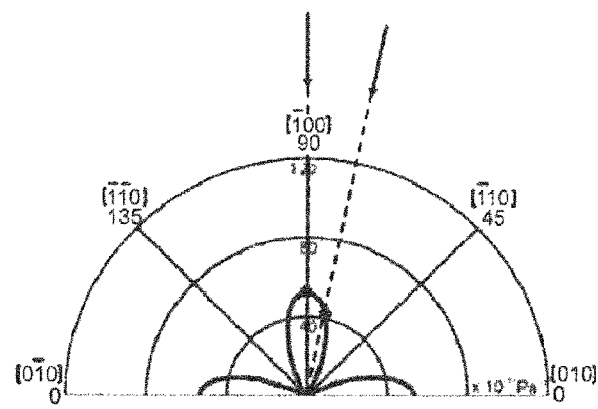
FIG. 5B is an angular diagram of stress sensitivity of a sensor that includes the monitoring device of FIG. 5A.

If the integrated sensor 10 were in direct contact with the concrete (for example, through a window in a traditional package), or were separated therefrom only by a thin passivation layer (for example, silicon), the integrated sensor 10 would directly detect a force exerted locally on a microscopic scale. In case the force, as illustrated above, would act along a different direction from the normal one, i.e., different from that of the crystalline axis of sensitivity of the sensor, the sensor sensitivity would decrease (as illustrated in FIG. 5B in the diagram of angular sensitivity of the sensor, in which the axes of the diagram refer to the orientation of the sensor 10 of FIG. 5A). Therefore, this would lead to an underestimation of the intensity of the force, thus determining an error, even a remarkable error, in the measurement of pressure.

On the contrary, the intermediation carried out by the package 15 made of building material may cause the various infinitesimal force contributions transmitted in a random and uneven manner by the concrete in the various points of the package surface to be substantially averaged out. By virtue of the properties of the package 15, illustrated above, the contributions averaged by the package 15 may result in a force applied by the package to the integrated sensor 10 in a direction normal thereto (such a force is indicated with an arrow F in FIG. 5A). Therefore, the fact that the sensor 10 "receives" the force through the package 15, with which it is in contact, and not directly from the concrete, allows the force to be detected in the direction in which the sensitivity is at a maximum, thus allowing the pressure to be correctly measured.

According to an embodiment, the integrated sensor 10 is a pressure or mechanical stress sensor, including a crystalline material having one or more predefined crystalline axes. Such a pressure or mechanical stress sensor may be capable of measuring the pressure or the mechanical stress which it is subjected to, along one of the crystalline axes, by exploiting the piezoresistive phenomenon in the silicon. The detectable quantity, transferred from the package 15 to the sensor 10, corresponds to an averaged combination of values assumed by the pressure or mechanical stress along the crystalline axis in different points of the solid structure portion in contact with the package 15.

In another embodiment, the integrated sensor 10 is a temperature sensor capable of measuring the temperature which it is subjected to by exploiting the phenomenon of the variations in the mobility in the silicon in dependence on the temperature. The detectable quantity, transferred from the package 15 to the sensor 10 corresponds to an averaged combination of values assumed by the temperature in different points of the solid structure portion in contact with the package 15.

Referring back to the functional diagram of the detection module 1 illustrated in FIG. 3, it is noted that it including functional blocks that, on the whole, constitute integrated circuitry 16. Such integrated circuitry, besides the sensor 10, further includes an integrated antenna 11.

The integrated antenna 11 performs the function of transmitting outside the integrated detection module 1, in a wireless mode, the measured data, i.e., the intensity of each of the electrical variables depending on and representative of, respectively, one of the physical quantities to be detected and monitored. The integrated antenna 11 further performs the function of receiving operating commands from the outside.

In a particular implementation example, the integrated antenna 11 performs the further function of receiving radiofrequency waves for a remote power feeding of the integrated module 1, without the need for batteries or power supplies in situ. The integrated antenna 11 is made to include at least one metallization level, for example, aluminum or copper, included in the chip forming the integrated detection module 1.

The integrated circuitry 16 further includes, as auxiliary blocks, a power supply circuit 12, a driving circuit 13, and a control circuit 14. The power supply circuit 12 is arranged to obtain the power supply for the operation of the integrated detection module 1 from radiofrequency waves received from the integrated antenna 11.

The driving circuit 13 is arranged to drive the integrated antenna 11 so that it wirelessly transmits the measured data. The control circuit 14 is arranged to control the operation of the integrated functional circuitry present in the integrated module 1 based upon operating commands sent from the exterior and received by the integrated antenna 11.

The power supply circuit 12, the driving circuit 13, and the control circuit 14 may be implemented by circuits per-se-known in the field of smart card production technologies, or of the RFID (Radio Frequency Identification) technology. For example, the integrated antenna 11 may operate based upon load modulation techniques. Such known aspects are not described in detail herein.

Figure 6:
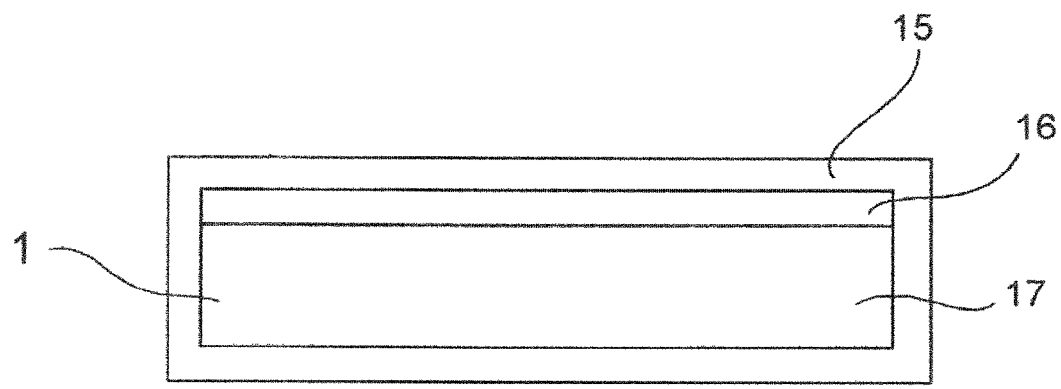
FIG. 6 is a sectional view of a package and of an integrated detection module included in a monitoring device according to another embodiment of the claimed invention.

Now, with reference to FIG. 6, some structural details of the integrated detection module 1 are to be noted. In the simplified sectional view of FIG. 6, a silicon sublayer 17 and an integrated circuitry portion 16 are schematically illustrated. The integrated functional circuitry portion 16 is schematized for sake of simplicity only by one layer, but it can, of course, be made by a plurality of layers, as it is well known.

The silicon sublayer 17 and the integrated functional circuitry portion 16 form the single chip on which the integrated detection module 1 is made. In accordance with a further particular embodiment, the chip of the integrated detection module 1 includes a further passivation layer, which may be made, for example, of silicon oxide, or silicon nitride, or silicon carbide.

The package 15, besides providing a mechanical protection, acts as an impermeable and protective layer against corrosion. In fact, as already described, such a package 15 is arranged to completely coat the chip on which the integrated detection module 1 is formed, and so that such module, as a whole, is entirely hermetically sealed and galvanically insulated from the surrounding environment.

It shall be noted that the complete sealing and the galvanic insulation are made possible by the fact that all the functionalities for the detection of the parameters to be monitored are realized by blocks that are present within the single chip, forming the integrated detection module 1. In particular, the integrated detection module 1, by virtue of the characteristics described above, is advantageously capable of providing its functions without any wire and/or metallization to provide the connections towards the outside of the integrated module itself. Therefore, it does not have any metal terminal, i.e., any wire bonding and/or pad and/or bump towards the outside, and thus it can be entirely sealed and galvanically insulated.

In particular, the package 15 may provide a complete protection of the integrated detection module 1 against water, humidity, and any other corrosion and degradation external agents, reducing the presence of weak points that can be etched by such agents, such as, for example, metallizations. Furthermore, with respect to the mechanical resistance and the pressure resistance, performance may be maintained by the fact that the package 15 is made of a building material, such as microsilica, which may be completely compatible with the material (for example, concrete) of the structure within which the device and the package have to be arranged.

These characteristics allow the integrated detection module 1 to be embedded in the structure to be monitored during the construction of the same structure, for example, during a casting step of liquid concrete. The characteristics further allow the integrated module 1 to subsequently operate from within the solid structure (for example, reinforced concrete) after the hardening of the concrete, having a long lifetime and good reliability parameters compared to the typical requirements.

Figure 7:
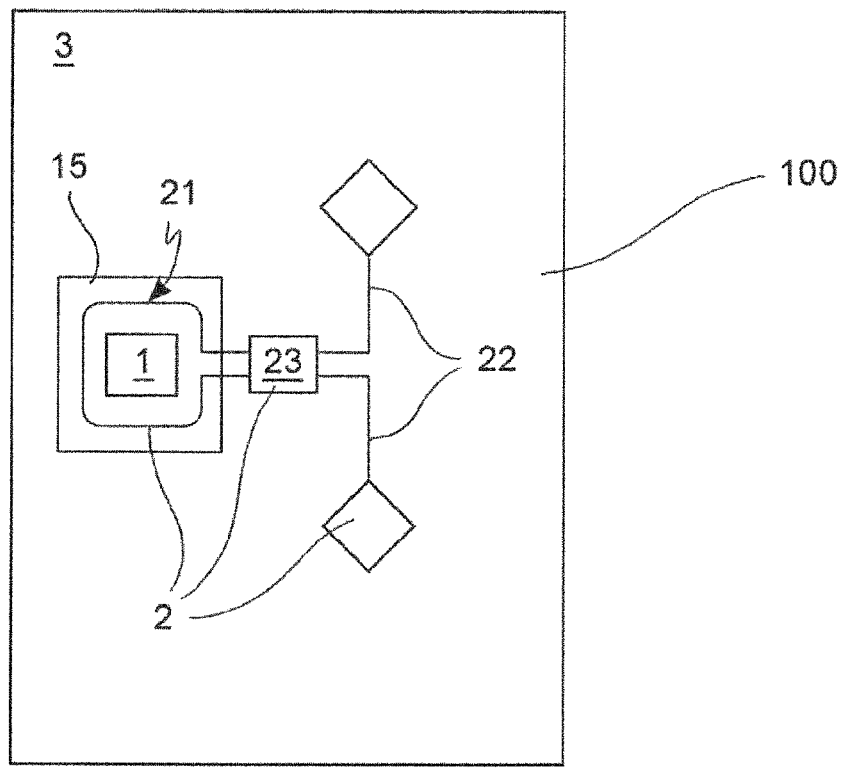
FIG. 7 is an operational block diagram of an electronic monitoring device according to another embodiment of the claimed invention.

Referring now to FIGS. 3 and 7, the electromagnetic means 2 or circuitry for transmitting/receiving electromagnetic signals and energy are considered in more detail. Such electromagnetic means 2 meet the desire to allow communication between the integrated detection module 1 and an external control and data collection system, remotely located, for example, at distances of some centimeter or some meters from the structure to be monitored, i.e., from the integrated detection module 1. This may involve transmitting near- or far-field electromagnetic energy, also taking into account the attenuations due to the solid structure through which the electromagnetic fields have to pass.

In view of this, the integrated antenna 11 included in the integrated detection module 1 typically cannot per se ensure a remote communication because of the intrinsic limits mainly due to its reduced dimensions. In the embodiment described herein, the electromagnetic means 2 allow, by virtue of the structure, both telecommunication signals to be transmitted/received (for example, transmitting measured data and receiving operating commands for the sensor), as well as an energy exchange to supply power (for example, receiving radiofrequency waves to supply power).

The electromagnetic means 2 perform an electromagnetic expansion and concentration function, i.e., they concentrate an external electromagnetic field, and its related energy, on the integrated antenna 11 of the integrated detection module 1. Similarly, the electromagnetic means 2 expand an electromagnetic field emitted by the integrated antenna 11, and its related energy, towards a remote antenna.

Figure 10:
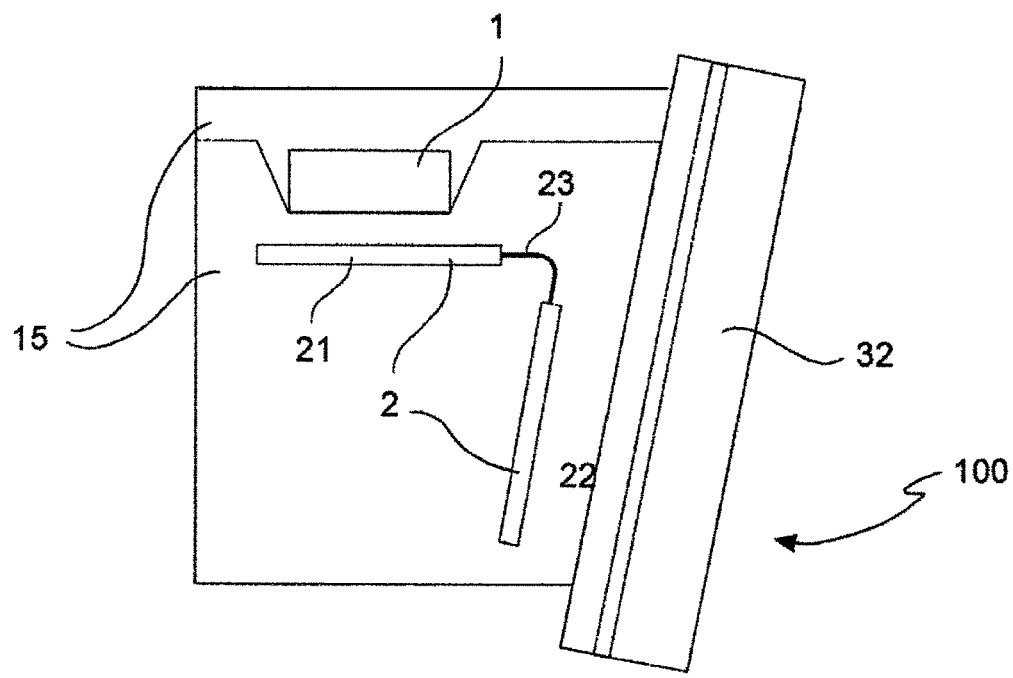

In particular, the electromagnetic means 2 include at least two antennas, a first antenna 21 and a second antenna 22, interconnected by connection means 23 or circuitry. Such connection means 23 can be, for example, a simple transmission line or another circuit (which may include, for example, a further electromagnetic expansion/concentration unit, as will be described below). It should be noted that, according to particular implementation examples (one of which is illustrated in FIG. 10), the first antenna 21 and the second antenna 22 may be inclined to each other at any angle between 0° and 180°, to correspondingly expand or concentrate electromagnetic energy in any directions.

The first antenna 21 communicates with the integrated antenna 11 of the integrated detection module 1 by electromagnetic fields (indicated by the symbol E in FIG. 3), and preferably by magnetic field coupling (i.e., near-field magnetic coupling). The second antenna 22 communicates with a remote antenna, for example of the control and data collection external system, by coupling of electromagnetic fields (i.e., far-field electromagnetic coupling). Each of the first and second antennas 21, 22 may be a magnetic dipole or a Hertzian dipole, or also another known type of antenna, provided it is capable of performing the above-described functions.

Now, FIG. 7 will be considered, which shows from a structural point of view a monitoring device 100 according to an embodiment. In particular, FIG. 7 illustrates a further embodiment of the electromagnetic means 2 and the package 15.

In the embodiment illustrated in FIG. 7, the first antenna 21 of the electromagnetic means 2 includes a coil 21. The connection means 23 of the electromagnetic means 2 may includes an adaptation circuit 23, per se known. The second antenna 22 of the electromagnetic means 2 comprises a Hertzian dipole antenna 22.

The coil 21 is located near the integrated detection module 1 and extends around it to magnetically couple with the integrated antenna 11. The currents induced by the integrated antenna 11 on the coil 21, acting as a magnetic dipole, are transferred to the Hertzian dipole antenna 22. Such transferring may be mediated by the adaptation circuit 23, which may allow improved overall performance of the electromagnetic means 2.

As noted before, the second antenna 22 is in this case a Hertzian dipole, suitable for far field communication. Therefore, the electromagnetic means 2 can be considered a hybrid transformer in which a Hertzian dipole is magnetically coupled to the integrated antenna 11.

Advantageously, the magnetic dipole, i.e., the coil 21, is designed as to reduce the dimensions thereof and optimize the coupling to the integrated antenna 11. Also advantageously, the Hertzian dipole, i.e., the antenna 22, is designed to optimize the far-field communication. In this regard, the dimensions of the Hertzian dipole antenna are typically comparable to the operative wavelength, which is related to the communication frequency.

According to an exemplary non-limiting implementation, the monitoring device 100 according to an embodiment can utilize a UHF transmission band, at frequencies of about 800 MHz or higher, which implies that it is provided with a Hertzian dipole of reasonable dimensions, on the order of centimeters. A wide range of frequency bands can be used in different embodiments, finding a balance, according to the specific applications, between the communication to be ensured, on one hand, and the size of the Hertzian dipole considered appropriate, on the other hand.

As noted before, the electromagnetic means 2 are capable, based on the same infrastructure already described, not only of transmitting and receiving telecommunications, but also of receiving energy from electromagnetic waves having a suitable power, at frequencies in the operative band of the Hertzian dipole antenna 22. The received energy is used for the remote power feeding of the detection module 1, via the power supply circuit 12.

Various further embodiments of the monitoring device will be now illustrated, with reference to different possible arrangements of the package 15. In accordance with a further embodiment, the device 100 is characterized in that the package 15 further coats at least one portion of the support means 3.

In particular, according to an implementation example, the package 15 coats a portion of the support means 3 containing the first antenna 21. Such implementation example is also illustrated in FIG. 7, and in FIG. 8 from a structural point of view.

Figure 9:
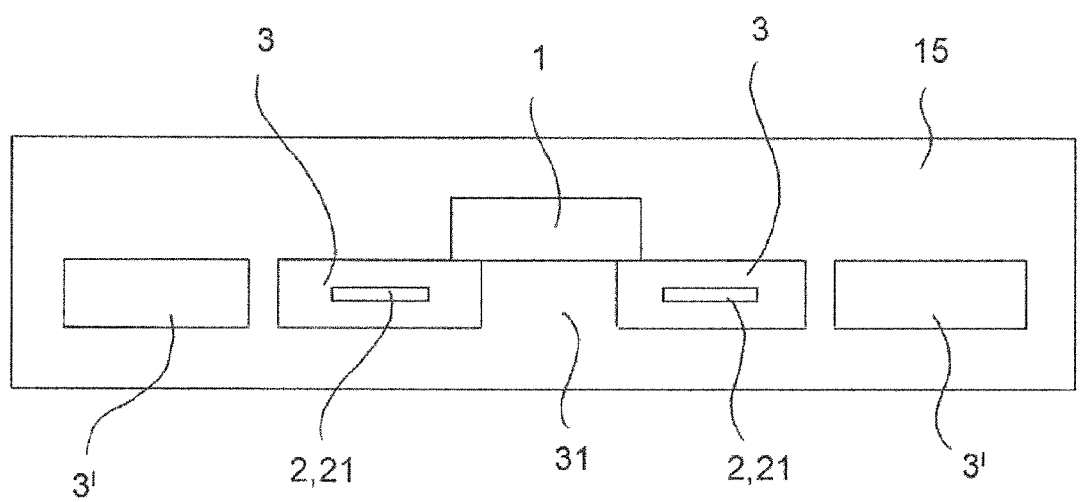

According to another implementation example, the package 15 coats a portion of the support means 3 including both the first antenna 21 and the second antenna 22 (as illustrated in FIG. 9). It shall be noted that the support portions including the first antenna 21 (sectional view) are indicated with the reference 3, and the support portions including the second antenna 22 (non visible in the view of FIG. 9) are indicated with the reference 3' in FIG. 9.

Figure 8:
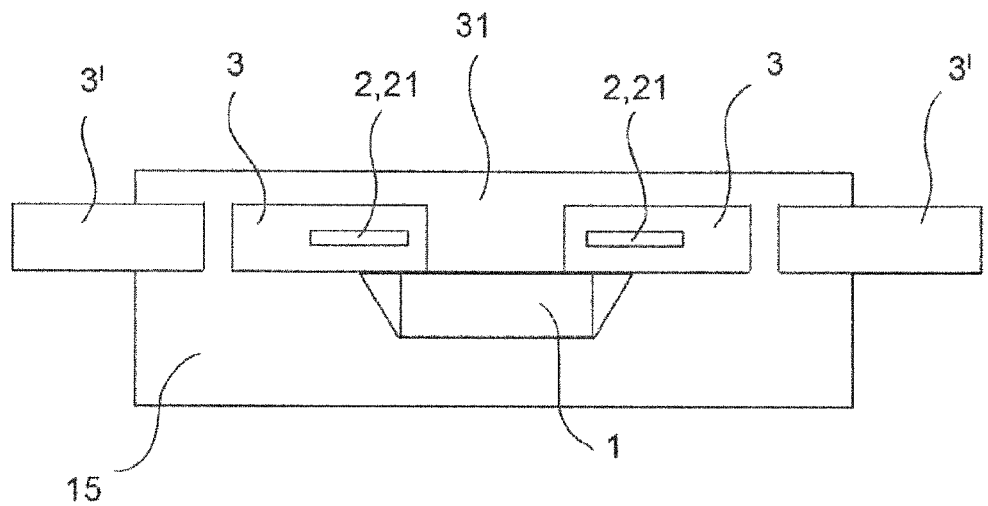
FIGS. 8-10 are sectional views of respective further embodiments of a monitoring device according to the claimed invention.

It is noted that, in the implementation examples illustrated in FIGS. 8 and 9, a hole 31 is advantageously provided in the support 3 at the position of the integrated sensor in the integrated detection module 1. Such a hole 31 is filled with the building material of the package 15, which can thus transfer in an optimal manner, a parameter to be measured by the sensor, according to the principles already described. In fact, by considering, for example a mechanical stress measurement, the presence of the hole 31 in the support 3 at the position of the sensor allows the building material of the package 15 to apply the same force on all the surfaces of the integrated detection module 1, and therefore the mechanical stress is accurately measured by the pressure sensor.

On the other hand, the desire to maximize the coupling between the integrated antenna 11 of the detection module 1 and the first antenna 21 of the electromagnetic means 2 may be taken into account. Accordingly, the thickness of the support 3 may be reduced as much as possible in the region in which such coupling occurs. Furthermore, as shown in FIGS. 8 and 9, the hole 31 of the support 3, filled with building material, can be obtained in the central part of the antenna 21 (visible in section) surrounding the integrated detection module 1. To further improve the magnetic coupling between the two antennas mentioned above, magnetic particles can be advantageously buried at least in a portion of the building material that forms the package 15 and that is contiguous to the two antennas 11 and 21.

According to further implementation examples (one of which is illustrated in FIG. 10), the package 15 fully coats the integrated detection module 1 and the electromagnetic means 2, whatever the nature and number of elements included in the latter is. In the examples set forth above, a portion 32 of the support means 3 for constraining the device 100 to a supporting structure (for example, the supporting structure 211 set forth in FIG. 16) remains uncoated by the package 1.

However, according to further embodiments, the package 15 completely coats the device 100. In such a case, the package 15 including the entire device 100 can be secured to the supporting structure 211 in several ways, for example by gluing or by using tie rods or clamps.

It is noted that different types of devices 100 can be entirely included in the package 15 according to the embodiments, for example a device in which the electromagnetic means 2 includes also at least one electromagnetic expansion and concentration unit 25. In particular, in the embodiment illustrated in FIG. 11, the connection means 23 of the electromagnetic means 2 includes a third antenna 251 connected through a first transmission line 231 to the first antenna 21, and a fourth antenna 252, connected through a second transmission line 232 to the second antenna 22. The third antenna 251 and the fourth antenna 252 are, in turn, configured to intercommunicate by, preferably, a magnetic coupling for near-field electromagnetic communication.

The fourth antenna 252, the second transmission line 232, and the second antenna 22 form the already mentioned electromagnetic expansion and concentration unit 25. The second antenna 22 and the fourth antenna 252 are inclined to each other at any angle between 0° and 180°, to expand or concentrate electromagnetic energy in any corresponding direction. In such embodiment, the package 15 coats a portion of the support means 3 also including the at least one electromagnetic expansion and concentration unit 25.

Figure 11:
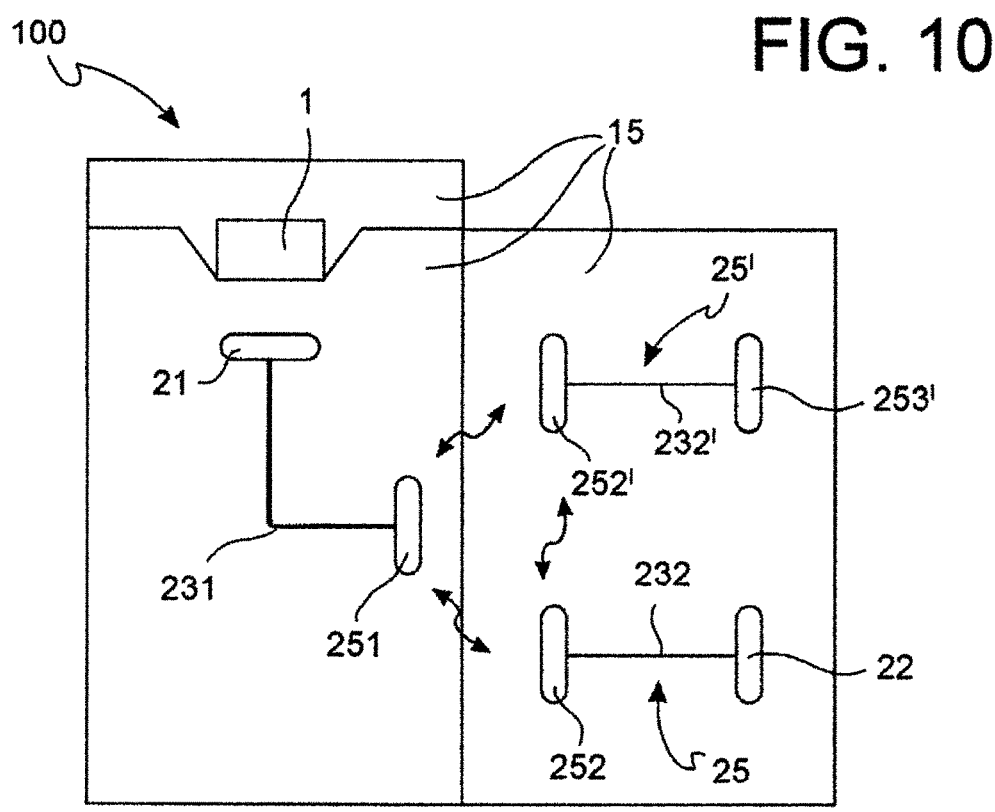

According to an implementation example, also illustrated in FIG. 11, the electromagnetic means 2 includes at least one further electromagnetic expansion and concentration unit 25' (structurally similar to the electromagnetic expansion and concentration unit 25) including a further fourth antenna 252', connected through a further second transmission line 232' to a further second antenna 253', and having the same characteristics of the second antenna 22. Advantageously, such further electromagnetic expansion and concentration unit 25' performs redundancy functions with respect to the unit 25 to enhance the reliability of the device, on the whole, which may thus increase its useful lifetime. To this aim, the further fourth antenna 252' is configured to communicate with the third antenna 251 or with the fourth antenna 252 by a magnetic coupling for near-field electromagnetic communication.

In accordance with another embodiment, the electromagnetic means 2 includes further electromagnetic expansion and concentration units, mutually arranged in cascade, and between the third antenna 251 and the fourth antenna 252. Similarly to what has been described above, each of the further electromagnetic expansion and concentration units includes a pair of antennas, in particular a fifth and a sixth antennas, interconnected via a transmission line, and such that one of the antennas is configured to communicate in a wireless mode with a corresponding antenna of a similar electromagnetic expansion and concentration unit arranged upstream. The other antenna is configured to communicate in a wireless mode with a corresponding antenna of a similar electromagnetic expansion and concentration unit arranged downstream.

The fifth antenna and the sixth antenna are inclined to each other at any angle between 0° and 180°, to expand or concentrate electromagnetic energy in any corresponding direction. By virtue of this, it may be possible to convey the signal generated by the detection module 1 also on relatively long distances to allow passage through a relatively wide thickness of solid structure in the case of sensors deeply buried in the structure.

In other implementation examples, different packages 15 may be provided. Each package may be configured to include one or more of the electromagnetic expansion and concentration units 25.

Figure 12:
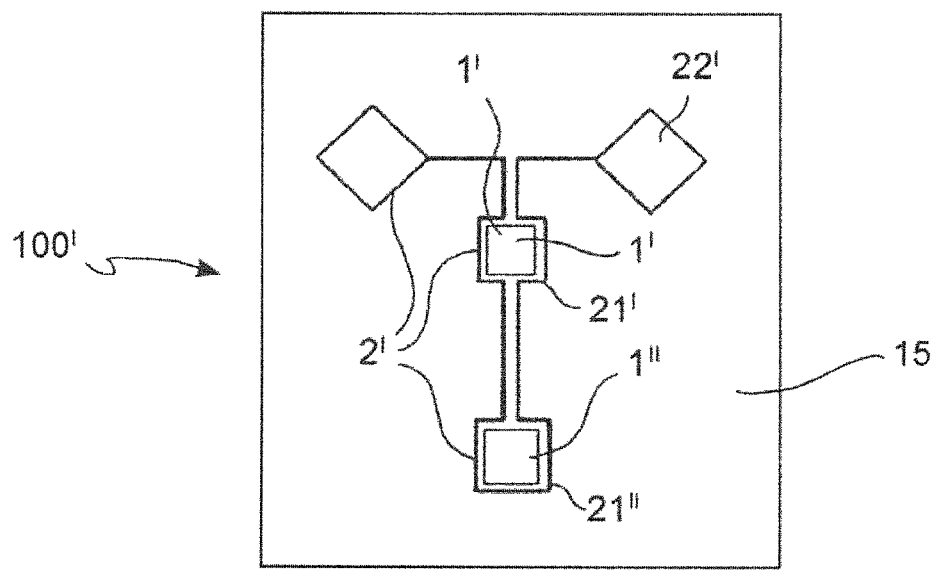

Advantageously, embodiments in which only one monitoring device includes a plurality of integrated detection modules are also possible. For example, a monitoring device 100' is illustrated in FIG. 12, including two integrated detection modules 1' and 1" and further including electromagnetic means 2' having three antennas: an antenna 22' for the far-field communication, and two antennas 21', 21", for the near-field communication. The antennas 21' and 21" may be suitable to communicate with the two different integrated detection modules 1', 1" included in the monitoring device 100', respectively.

The antennas 21' and 21" for the near field communication may be implemented, respectively, for example, by a coil 21' and a further coil 21", arranged in a cascade configuration. The antenna 21' may be a quadrupole formed in the specific example by two semi-coils. The coil 21' may be directly connected to the antenna 22', and the further coil 21" may be connected to the antenna 22' via the coil 21'.

Such an approach can be advantageously applied in the case where two integrated detection modules are used in the same monitoring device, one of which is redundant, so that the operation may not be jeopardized in case of damage of one of the two integrated detection modules, in which case the redundant integrated detection module will be used. Such an approach may also be applied in the case where the two integrated detection modules 1', 1" are two mutually independent modules provided an expedient to reduce collisions between the communications relating to the two modules is used. For example, a suitable communication protocol may be applied for reducing the occurrence of message collisions, as it is known, for example, in the RFID field or by distinguishing the transmission frequencies of the two different integrated detection modules 1', 1", or by codifying in a different manner the messages for the two different integrated detection modules 1', 1". The package 15 coats the entire monitoring device 100'. According to a further embodiment, the antennas 21' and 21", instead of being cascade coupled to each other, may be connected in parallel.

In accordance with further implementation examples, as shown for example in FIGS. 14A and 14B, the monitoring device 100' includes a plurality of integrated detection modules and a corresponding plurality of antennas, for example coils, for near-field communication. Each of the connections between such antennas for near-field communication can be in cascade, or in parallel, according to any combinations. The package 15 completely coats the plurality of integrated detection modules and the corresponding plurality of antennas.

With reference to FIG. 14B, a particular implementation example is illustrated in which the device 100' includes two end antennas 22' and 22", at the ends of the cascade of antennas 21 of the electromagnetic means 2' on the support 3. Such end antennas can be configured to communicate with a remote antenna, via a far-field electromagnetic coupling, or to communicate, preferably by a magnetic coupling, with corresponding end antennas of similar devices 100' arranged in cascade.

It is noted that, in the implementation example of FIG. 14B, by applying a suitable torque to the support 3 before forming the package 15, a helicoidal shape can be determined for such support 3. In this way, the different integrated detection modules 1 can be advantageously oriented differently, allowing each integrated detection module 1 to measure at least one parameter according to a different direction with respect to the other integrated detection modules that are contiguous thereto.

Figure 13:
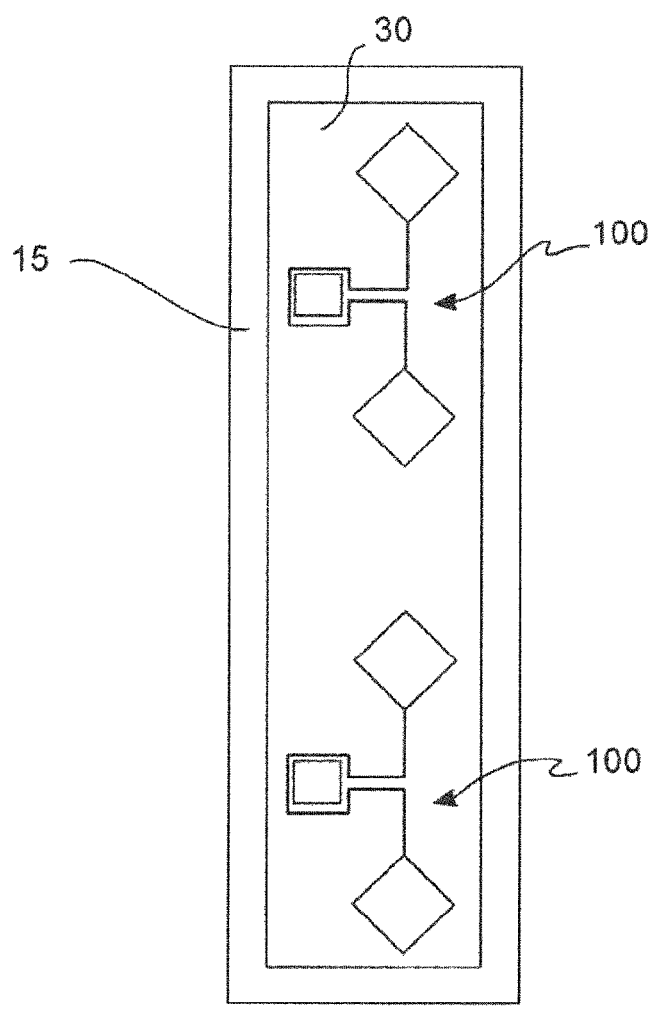

According to alternative embodiments, which are illustrated in FIGS. 15A and 15B, each integrated detection module 1 can be encapsulated in a pre-package 15' made of building material similar to the package 15, according to a corresponding predefined orientation. Such predefined orientation can be obtained by orienting the pre-package 15' according to one or more markers 159' that are present on the support 3 and in accordance with the possible markers 159 indicating the orientation of the integrated detection module 1 included in the pre-package 15' (example illustrated in FIG. 15A), or by providing an opening 33 in the support 3, which has its own orientation, corresponding to the desired one, and suitable to house the pre-package 15' including the integrated detection module 1 (this example is illustrated in FIG. 15B). In a further embodiment, the package 15 fully coats a plurality of devices 100 placed on a common support 30, as shown in FIG. 13.

The above-described examples, in which the package 15 fully coats a monitoring device 100, or a plurality of monitoring devices 100, can be formed, from a structural point of view, in different ways providing for particular configurations of the package 15, particularly suitable to specific applications. For example, the package 15 can be conformed to be insertable in a corresponding recess within the solid structure 300 to be monitored. This may be particularly useful for monitoring devices to be used in ceilings or beams, in slabs, or also in piles for bridges or piling structures. In such a case, by suitably combining the integrated modules including the sensors, the corresponding antennas, and optionally the electromagnetic expansion and concentration units, measurements at predefined points in the structure may be obtained. And data can be transferred to antennas arranged in the proximity of an external zone to which the measurement data have to be sent.

According to another example, the package 15 is shaped to be insertable in a nail or a expansion screw. The nail or the expansion screw are, in turn, suitable to be fixed in the solid structure to be monitored. This embodiment may be particularly useful for monitoring structures of already existing buildings, for example, historical buildings. In an implementation example of the nail, the nail may be formed by electromagnetic means or circuitry having an electromagnetic expansion and concentration function, and an optional further electromagnetic expansion and concentration units arranged on a flexible support, which is bent and housed in the package made of building material together with an integrated detection module (in turn, optionally included in a further package made of building material).

To insert such nail in the structure to be monitored, a recess is formed therein, in which building material in a semisolid form is then injected. The nail is inserted within such building material (preferably a quick-setting material, thus intended to harden after the insertion of the nail) by using techniques and tools that are known in the building construction field, such as, for example, rubber hammers or compressed air guns that may be suitably modified to house such a nail.

Figure 16:
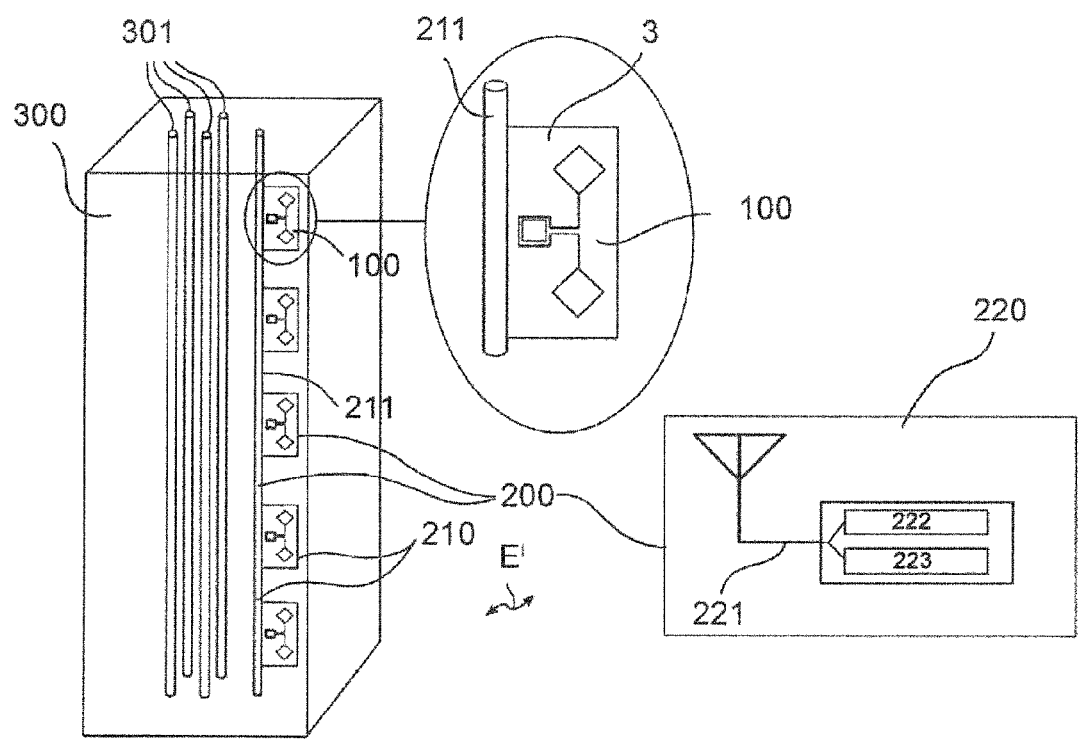
FIG. 16 is a diagram of a system for monitoring local parameters within a solid structure according to an embodiment of the claimed invention.

A system 200 for monitoring parameter within a solid structure is considered with reference to FIG. 16, in which the monitoring device 100 and the package 15 described above are employed. The monitoring system 200 is capable of monitoring one or more parameters in one or in a plurality of points ("local" parameters), within a solid structure 300 to be monitored.

It should be noted that the illustration of FIG. 16, given by way of illustrative example only, is not in scale. In particular, for sake of illustrative clarity, the relative dimensions of the monitoring devices 100 are enlarged therein.

The monitoring system 200 illustrated in FIG. 16 includes an internal monitoring subsystem 210 arranged within the solid structure 300, and an external control and data collection subsystem 220 arranged externally and remotely with respect to the solid structure 300. The internal monitoring subsystem 210 includes a supporting structure 211 passing through the points to be monitored within the solid structure 300, and further includes a plurality of monitoring devices 100 according to the present embodiments. Each of the monitoring devices 100 is secured to the supporting structure 211 in a known and predefined position.

In the example of FIG. 16, the structure to be monitored is a reinforced concrete pillar 300 including reinforcing steel rods 301. Therefore, the internal monitoring subsystem 210 is included within such reinforced concrete pillar, starting from the construction step thereof. In the construction step, the internal monitoring subsystem 210 is suitably arranged in a desired position within the volume defined by a formwork. Subsequently, liquid concrete is poured into the formwork, thus surrounding the internal monitoring subsystem 210 and embedding it upon hardening so that such subsystem is finally "buried" within the reinforced concrete pillar.

The supporting structure 211 may provide support and secure each of the monitoring devices 100 in a known and predefined position. Such supporting structure 211 extends within the solid structure 300.

In the example of FIG. 16, the supporting structure 211 is a plumb-line, and extends in a rectilinear manner along one dimension of the pillar 300. In other embodiments, the supporting structure 211 can be of any shape, for example rectilinear along another dimension, broken, semicircular, generically curvilinear, or other shape. The criteria with which such shape is determined may depend on the shape of the structure to be monitored, for example, a curvilinear shape may be suitable to the curvilinear shape of the vault of a tunnel.

It is noted that the shape and positioning of the supporting structure 211 may determine the geometrical development of the internal monitoring subsystem 210, which may be characterized by a very wide range of variations. The criteria with which the geometrical development of the internal monitoring subsystem 210 is determined, in the different embodiments, may depend on the shape of the structure to be monitored and the selection of the significant points to be monitored within the same structure (for example, along one or more axes of the structure, or in points that are particularly sensitive from the structural point of view).

The materials of which the supporting structure 211 is made can be various, for example, metallic or synthetic. Again, it is noted that the supporting structure 211, therefore the geometrical development of the internal monitoring subsystem 210, may include several parts which are not interconnected, and each of which has the characteristics listed above.

At least one of the monitoring devices 100 according to the present embodiments are connected to the supporting structure 211 via the support 3. Each of the monitoring devices 100 is secured to the supporting structure 211 in a known and predefined position. In particular, the support 3 can be glued or mechanically constrained to the supporting structure 211 in any known way.

According to an alternative embodiment, already shown in FIG. 13 above, a polymeric material support strip 30 is provided to be secured to the supporting structure 211, and suitable to house a plurality of monitoring devices 100 at predefined distances and in predefined positions. On a support strip 30, such as the one illustrated in FIG. 13, it may be possible to place monitoring devices 100 having several types of electromagnetic means 2 different from one another.

For example, electromagnetic expansion and concentration elements for far-field communication and electromagnetic expansion and concentration elements for near-field communication can be present. Furthermore, the electromagnetic expansion and concentration elements for far-field communication can have different orientations to account for the different possible directions at which the electromagnetic signal are received, coming from systems that are external to the solid structure. Therefore, the antennas of such electromagnetic expansion and concentration devices can be, for example, vertically biased antennas, horizontally biased antennas, and/or antennas orientated according to different angles.

Referring again to the monitoring system 200 illustrated in FIG. 16, the external control and data collection subsystem (or "external subsystem" 220) will be now illustrated. The external subsystem 220 may advantageously be located in a suitable position where the installation is relatively easy, and also at a certain distance from the structure to be monitored 300 provided that such distance allows the communication with the internal monitoring subsystem 210 and the operation thereof. Such external subsystem is per se known, and therefore it is described herein briefly.

The external subsystem 220 includes one or more external antennas 221, data collection, storage, and processing means 222 or circuitry, and power supplying and remote supplying means 223 or circuitry.

The external antenna 221 is capable of communicating with each of the electromagnetic means 2 of each of the monitoring devices 100 included in the internal monitoring subsystem 210 to thereby implement the already illustrated exchange of telecommunications signals and energy via electromagnetic fields. Through the external antenna 221, the external subsystem 220 receives the data sent by one or any of the plurality of devices 100 of the internal monitoring subsystem 210 representative of one or more parameters detected and measured by the corresponding sensors 10. The received data are forwarded to the data collection, storage, and processing means 222 or circuitry.

Furthermore, via the antenna 221, the external subsystem 220 sends control signals, for example, commands, to one or any of the plurality of devices 100 of the internal monitoring subsystem 210. Such control signals act, for example, to configure a predefined device 100, and/or for the measurement of a predefined parameter (at a predefined time or continuously), or other control, configuration, or remote maintenance functions. For the above-mentioned functions, it may also be possible to use communication modes and telecommunication protocols per se known (for example, in the RFID field).

Finally, again via the antenna 221, the external subsystem 220 sends electromagnetic energy, for example in the form of radiofrequency electromagnetic waves, for the remote power supply of one or any plurality of devices 100 of the internal monitoring subsystem 210. The data collection, storage, and processing means 222 or circuitry can be implemented by one or more processors, which are physically located together with the other elements of the external subsystem 220, or also arranged remotely and mutually connected via any telecommunications network.

Many different types of processing operations can be performed by such processors, for example, but not limited to: monitoring of the spatial profile of different parameters, with or without interpolation; monitoring of the temporal and historical trends of different parameters; comparison with thresholds to determine possible degradation and danger conditions; and so on. The power supplying and remote supplying means 223 or circuitry may include different types of energy generators, for example solar cells, fuel cells, or rechargeable batteries.

Further embodiments of a monitoring system include the direct insertion of one or a plurality of units into the structure to be monitored. The units include a package made of building material that coats one or a plurality of monitoring devices, for example, in the form of one of the already mentioned nails or expansion screws, including one or more monitoring devices entirely contained and coated by a package made of building material.

Figure 17:
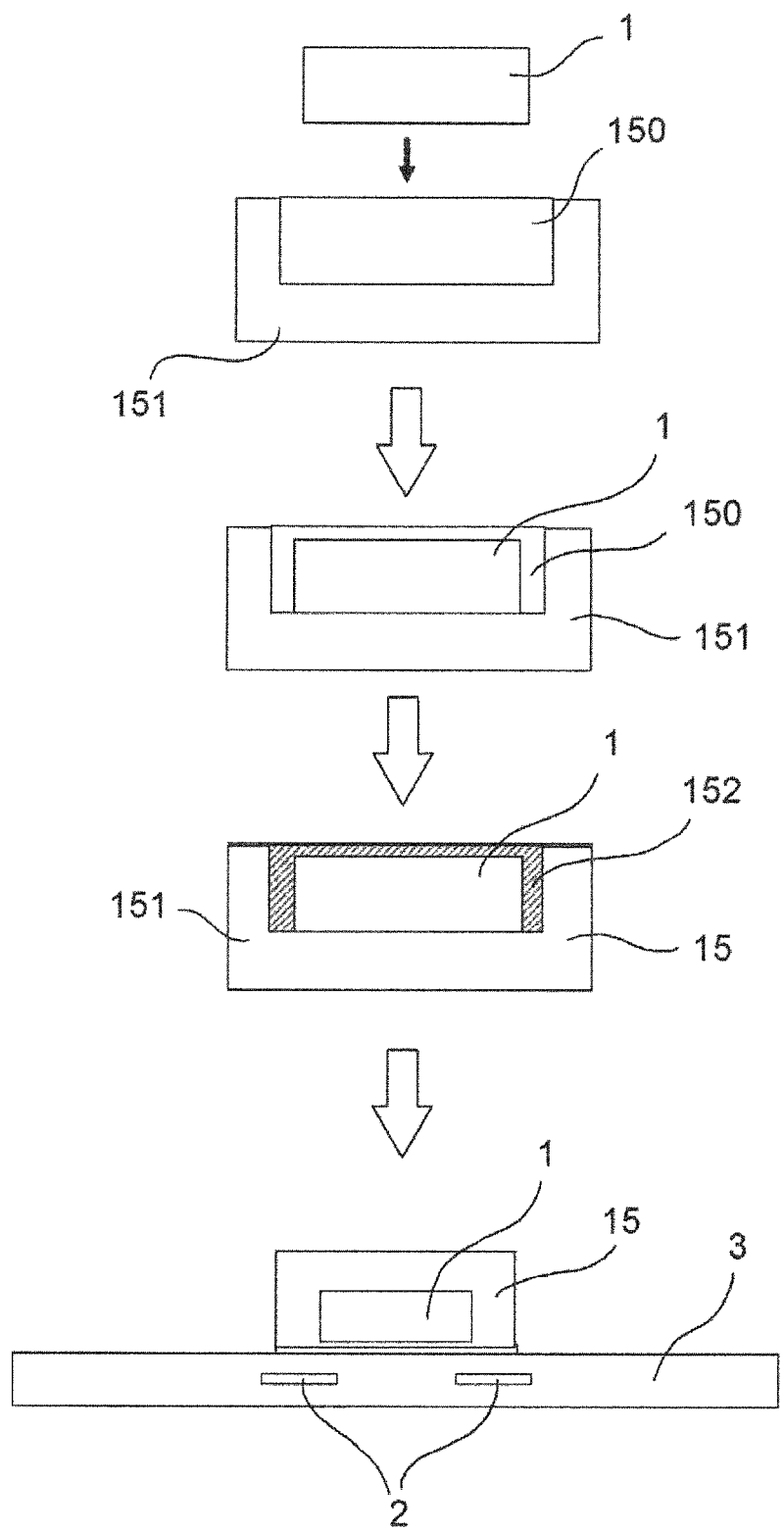
FIGS. 17 and 18 are diagrams of package manufacturing method and a monitoring device manufacturing method, respectively, according to an embodiment of the claimed invention.
Figure 18:
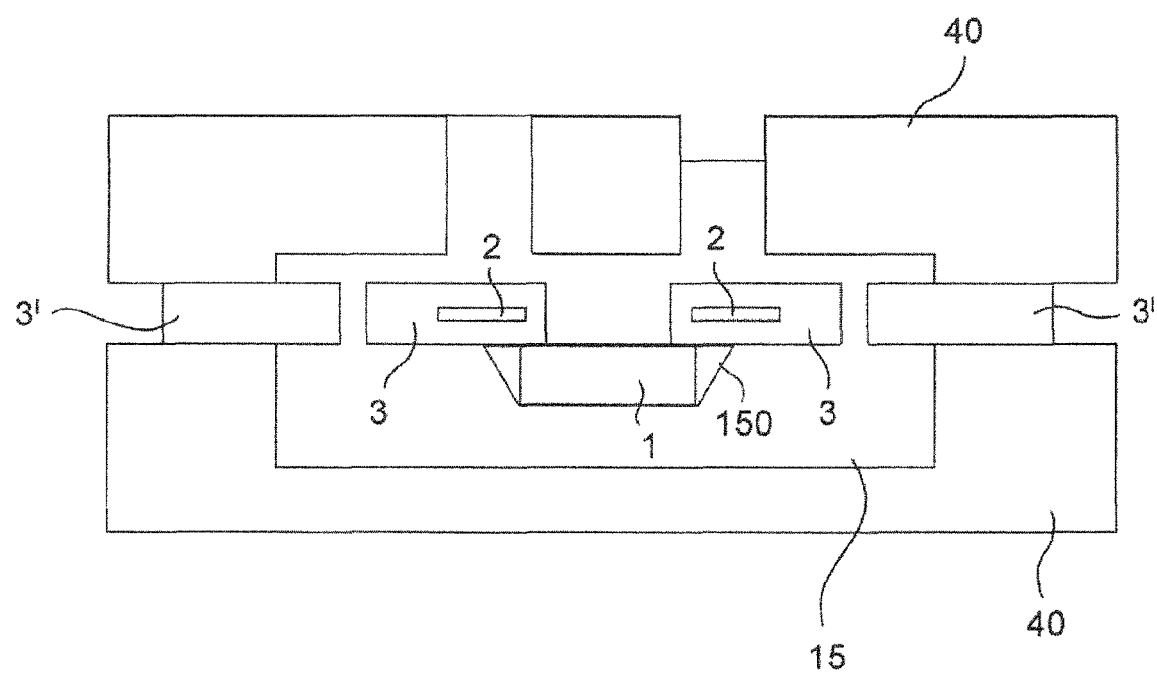

With reference to FIGS. 17 and 18, a method for manufacturing a device 100 for detecting and monitoring one or more local parameters within a solid structure 300 will be now described. Such a method includes producing a housing portion 151 by using a building material formed of particles of micrometric or sub-micrometric dimensions, in which housing portion a housing 150 is arranged. The method also includes inserting an integrated detection module 1 of the device 100 into the housing 150, and forming a filling portion 152 by using building material made of particles of micrometric or sub-micrometric dimensions to produce a package 15 so arranged as to completely coat the integrated detection module 1. The method also includes securing the package 15 to support means 3 of the device 100 configured to further support electromagnetic means 2 of the device 100, and further configured so as to fix the device 100 to a supporting structure passing through the points to be monitored within the solid structure.

According to a further implementation example, illustrated in FIG. 18, the method also includes producing a further portion of package around a further portion of the device 100 with respect to the integrated detection module 1 by injection of building material made of particles of micrometric or sub-micrometric dimensions into a mold 40. In particular, after arranging the integrated detection module in the corresponding housing 150, the support 3 may be placed on the portion of the already formed package, and the package 15 may be completed by further building material of the same type, in portions that are determined by the mold 40 to include any portion of the device according to any of the already described embodiments of the device. In particular, inter alia, the housing 150, in which the integrated detection module 1 is located, is filled.

Recesses or holes may be located in the support 3 to connect the various portions of the package, thus making it, on the whole, more robust. The presence of such holes or recesses further allows the drainage of air, water, and water vapor that may be present in the building material. Advantageously, to reduce the formation of recesses and non-homogeneities within the package, the mold can be shaken to facilitate the escape of gases that may be present in the mold itself.

In accordance with a further exemplary implementation, the method further includes aligning the housing portion 151 and the filling portion 152 of the package 15, for example, by simple mechanical guides. According to a further embodiment of the method, the method may include, before inserting the integrated detection module 1 into the housing 150, encapsulating the integrated detection module 1 in a pre-package made of building material.

In fact, the building material package of the present embodiments may allow an accurate measurement of the local parameters to be monitored, while ensuring that the monitoring device is relatively simple, robust, and reliable, capable of resisting the pressures and temperatures present within a solid structure to be monitored, both in the construction step, and during its corresponding operative life, and further particularly resistant against the main degradation causes, such as, for example, those due to water and humidity. The package, being made of a material similar to that used for the building structure may be completely compatible with the same structure. Meanwhile, the building material of the package, for example, made at least partially of microsilica, is also compatible with the silicon sublayer of the chip on which the integrated detection module 1 of the device 100 is formed. Furthermore, the shape of the package 15, according to the present embodiments can be any shape, thus fitting a wide range of applications.

To the above-described embodiments of the package, the monitoring device, the monitoring system, and the manufacturing method, those of ordinary skill in the art, to meet contingent desires, will be able to make modifications, adaptations, and replacements of elements with other functionally equivalent ones, also in combination with the prior art, also generating hybrid implementations, without departing from the scope of the following claims. Each of the characteristics described as belonging to a possible embodiment can be implemented independently from the other embodiments described.

The invention claimed is:

1. A package for a device configured to detect at least one local parameter in a solid structure comprising:
a housing comprising a plurality of cement particles and a plurality of silica particles joined together, said plurality of cement particles and said plurality of silica particles having a dimension less than or equal to 10 microns.

2. The package according to claim 1, wherein said plurality of silica particles has a dimension less than or equal to 1 micron.

3. The package according to claim 1, wherein said package is isotropic on a millimetric scale.

4. The package according to claim 1 wherein said plurality of silica particles comprises microsilica particles.

5. The package according to claim 1, wherein the device comprises an integrated detection module; wherein said housing has a recess therein configured to receive said integrated detection module therein; and wherein said housing comprises a filling within the recess and configured to surround said integrated detection module.

6. The package according to claim 5, wherein said housing is configured to be rotated with respect to an axes system of the package to determine a predefined positioning of the integrated detection module to detect the at least one local parameter along a corresponding predefined direction relative to the predefined positioning.

7. A device for detecting at least one local parameter within a solid structure comprising:
an integrated detection module comprising at least one integrated sensor configured to detect the at least one parameter; and
a package configured to cover said integrated detection module;
said package comprising a plurality of cement particles and a plurality of silica particles joined together, said plurality of cement particles and said plurality of silica particles having a dimension less than or equal to 10 microns.

8. The device according to claim 7, wherein said package has an internal surface in contact with said at least one integrated sensor, and has an external surface in contact with the solid structure, the internal and external surfaces defining a separation between said at least one integrated sensor and the solid structure and configured to allow the transfer of at least one detectable quantity related to the at least one local parameter to said at least one integrated sensor.

9. The device according to claim 7, wherein said at least one integrated sensor is configured to detect the at least one parameter selected from the group of pressure, temperature, and mechanical stress.

10. The device according to claim 9, wherein said integrated sensor comprises at least one temperature sensor configured to measure a temperature based upon variations in a mobility of silicon based upon temperature values at a plurality of different points of contact between the solid structure and said package.

11. The device according to claim 9, wherein said at least one integrated sensor comprises a pressure sensor comprising a crystalline material having at least one crystalline axis, said pressure sensor being configured to measure a pressure along the at least one crystalline axis based upon piezoresistivity of silicon based upon a pressure along the at least one crystalline axis and at plurality of different points of contact between the solid structure and said package.

12. The device according to claim 9, wherein said at least one integrated sensor comprises a mechanical stress sensor comprising a crystalline material having at least one crystalline axis, said mechanical stress sensor being configured to measure a mechanical stress along the at least one crystalline axis based upon piezoresistivity of silicon based upon a mechanical stress along the at least one crystalline axis and at plurality of different points of contact between the solid structure and said package.

13. The device according to claim 7, wherein said integrated detection module further comprises an integrated antenna coupled to said at least one integrated sensor to define a single integrated circuit (IC) chip; and wherein said package surrounds said single IC chip.

14. The device according to claim 13, further comprising:
electromagnetic circuitry configured to communicate between said integrated antenna and a remote antenna, said integrated antenna, electromagnetic circuitry, and the remote antenna being configured to communicate via at least one of a magnetic and electromagnetic coupling; and
a support configured to provide support to said integrated detection module and said electromagnetic circuitry, and further configured to fix the device to a supporting structure passing through points to be monitored within the solid structure;
said package covering at least a portion of said support.

15. The device according to claim 14, wherein said electromagnetic circuitry comprises:
a first antenna configured to communicate with said integrated antenna via a magnetic coupling for near-field electromagnetic communication;
a second antenna configured to communicate with the remote antenna via a far-field electromagnetic communication; and
connection circuitry configured to connect said first antenna and said second antenna;
said package covering a portion of the support including said first antenna.

16. The device according to claim 15, wherein said first antenna and said second antenna are configured to be inclined to each other at an angle between 0° and 180°.

17. The device according to claim 15, wherein said connection circuitry further comprise:

a third antenna and a first transmission line coupled thereto, said first transmission line connected to said first antenna; and a fourth antenna and a second transmission line coupled thereto, said second transmission line connected to said second antenna, and said second and fourth antennas and said second transmission line defining an electromagnetic expansion and concentration unit;

said third antenna and said fourth antenna being configured to communicate via a magnetic coupling for near-field electromagnetic communication;

said first antenna and said third antenna being inclined to each other at an angle between 0° and 180°;

said second antenna and said fourth antenna being inclined to each other at an angle between 0° and 180°;

said package covering a portion of the support including said at least one electromagnetic expansion and concentration unit.

18. The device according to claim 17, wherein said connection circuitry comprises at least one further electromagnetic expansion and concentration unit between said third antenna and said fourth antenna, said at least one further electromagnetic expansion and concentration unit comprising a fifth antenna and a sixth antenna coupled to said fifth antenna and configured to communicate, via a magnetic coupling for near-field electromagnetic communication, respectively, with one of the fourth and second antennas of said electromagnetic expansion and concentration unit arranged in cascade upstream from said at least one further electromagnetic expansion and concentration unit, and an antenna of another electromagnetic expansion and concentration unit arranged in cascade downstream from said at least one further electromagnetic expansion and concentration unit; said fifth antenna and said sixth antenna being inclined to each other at any angle between 0° and 180°, based upon an inclination of a corresponding antenna connected via a wireless coupling; and said package covering a portion of said support including said at least one further electromagnetic expansion and concentration unit.

19. The device according to claim 14, further comprising at least one further integrated detection module carried within said support and comprising a further integrated antenna; and wherein said electromagnetic circuitry comprises:

a first antenna comprising a coil configured to communicate with said integrated antenna of said integrated detection module via a magnetic coupling for near-field electromagnetic communication; and at least one corresponding further first antenna comprising a further coil configured to communicate with said further integrated antenna via a magnetic coupling for near-field electromagnetic communication;

said coil and said further coil being mutually operatively coupled in one of cascade, in parallel, and in series;

said package covering a portion of said support including said further integrated detection module and said electromagnetic circuitry.

20. The device according to claim 14, wherein said package is configured to be insertable into a corresponding recess within the solid structure to be monitored.

21. The device according to claim 14, wherein said package is configured to be insertable into at least one of a nail and an expansion screw; the at least one of the nail and the expansion screw being configured to be fixed into the solid structure to be monitored.

22. A system for monitoring at least one parameter in a plurality of points within a solid structure, the system comprising:

an internal monitoring subsystem carried within the solid structure; and an external control and data collection subsystem remote from the solid structure;

said internal monitoring subsystem comprising a supporting structure passing through the plurality of points, and a plurality of monitoring devices coupled to the supporting structure and comprising an integrated detection module comprising at least one integrated sensor configured to detect the at least one parameter, and a package configured to cover said integrated detection module, said package comprising a plurality of cement particles and a plurality of silica particles joined together, said plurality of cement particles and said plurality of silica particles having a dimension less than or equal to 10 microns.

23. The system according to claim 22, wherein said at least one integrated sensor is configured to detect the at least one parameter selected from the group comprising pressure, temperature, and mechanical stress.

24. The system according to claim 23, wherein said at least one integrated sensor comprises at least one temperature sensor configured to measure a temperature based upon variations in a mobility of silicon based upon temperature values at a plurality of different points of contact between the solid structure and said package.

25. The system according to claim 23, wherein said at least one integrated sensor comprises a pressure sensor comprising a crystalline material having at least one crystalline axis, said pressure sensor being configured to measure a pressure along the at least one crystalline axis based upon piezoresistivity of silicon based upon a pressure along the at least one crystalline axis and at plurality of different points of contact between the solid structure and said package.

26. The system according to claim 23, wherein said at least one integrated sensor comprises a mechanical stress sensor comprising a crystalline material having at least one crystalline axis, said mechanical stress sensor being configured to measure a mechanical stress along the at least one crystalline axis based upon piezoresistivity of silicon based upon a mechanical stress along the at least one crystalline axis and at plurality of different points of contact between the solid structure and said package.

27. The system according to claim 22, wherein said integrated detection module further comprises an integrated antenna coupled to said integrated sensor to define a single integrated circuit (IC) chip; and wherein said package completely surrounds said single IC chip.

28. The system according to claim 27, wherein each of said plurality of monitoring devices further comprises:

electromagnetic circuitry configured to communicate between said integrated antenna and a remote antenna, said integrated antenna, electromagnetic circuitry, and the remote antenna being configured to communicate via at least one of a magnetic and electromagnetic coupling; and a support configured to provide support to said integrated detection module and said electromagnetic circuitry, and further configured to fix the device to a supporting structure passing through points to be monitored within the solid structure;

said package covering at least a portion of said support.

29. The system according to claim 28, wherein said electromagnetic circuitry comprises:
a first antenna configured to communicate with said integrated antenna via a magnetic coupling for near-field electromagnetic communication;
a second antenna configured to communicate with the remote antenna via a far-field electromagnetic communication; and
connection circuitry configured to connect said first antenna and said second antenna;
said package covering a portion of the support including said first antenna.

30. The system according to claim 29, wherein said first antenna and said second antenna are configured to be inclined to each other at an angle between 0° and 180°.

31. The system according to claim 29, wherein said connection circuitry further comprises:
a third antenna and a first transmission line coupled thereto, said first transmission line connected to said first antenna; and
a fourth antenna and a second transmission line coupled thereto, said second transmission line connected to said second antenna, and said second and fourth antennas and said second transmission line defining an electromagnetic expansion and concentration unit;
said third antenna and said fourth antenna being configured to communicate via a magnetic coupling for near-field electromagnetic communication;
said first antenna and said third antenna being inclined to each other at an angle between 0° and 180°;
said second antenna and said fourth antenna being inclined to each other at an angle between 0° and 180°;
said package covering a portion of the support including said at least one electromagnetic expansion and concentration unit.

32. The system according to claim 31, wherein said connection circuitry comprises at least one further electromagnetic expansion and concentration unit between said third antenna and said fourth antenna, said at least one further electromagnetic expansion and concentration unit comprising a fifth antenna and a sixth antenna coupled to said fifth antenna and configured to communicate, via a magnetic coupling for near-field electromagnetic communication, respectively, with one of the fourth and second antennas of said electromagnetic expansion and concentration unit arranged in cascade upstream from said at least one further electromagnetic expansion and concentration unit, and an antenna of another electromagnetic expansion and concentration unit arranged in cascade downstream from said at least one further electromagnetic expansion and concentration unit; said fifth antenna and said sixth antenna being inclined to each other at any angle between 0° and 180°, based upon an inclination of a corresponding antenna connected via a wireless coupling; and said package covering a portion of said support including said at least one further electromagnetic expansion and concentration unit.

33. The system according to claim 29, wherein each of said plurality of monitoring devices further comprises at least one further integrated detection module carried within said support and comprising a further integrated antenna; and wherein said electromagnetic circuitry comprises:
a first antenna comprising a coil configured to communicate with said integrated antenna of said integrated detection module via a magnetic coupling for near-field electromagnetic communication; and
at least one corresponding further first antenna comprising a further coil configured to communicate with said further integrated antenna via a magnetic coupling for near-field electromagnetic communication;
said coil and said further coil being mutually operatively coupled in one of cascade, in parallel, and in series;
said package covering a portion of said support entirely including said further integrated detection module and said electromagnetic circuitry.

34. The system according to claim 29, wherein said package is configured to be insertable into a corresponding recess within the solid structure to be monitored.

35. The system according to claim 29, wherein said package is configured to be insertable into at least one of a nail and an expansion screw; the at least one of the nail and the expansion screw being configured to be fixed into the solid structure to be monitored.

36. A method of making a device for detecting at least one local parameter in a solid structure, the method comprising:
forming a housing using a building material comprising a plurality of cement particles and a plurality of silica particles joined together, the plurality of cement particles and the silica particles having a dimension less than or equal to 10 microns;
positioning an integrated detection module of the device into the housing;
forming, using the building material, a filling to define a package that covers the integrated detection module; and
coupling the package to a support configured to support electromagnetic circuitry and configured to fix the device to a supporting structure passing through a plurality of points to be monitored within the solid structure.

37. The method according to claim 36, further comprising forming a further package portion around a further portion of the device with respect to the integrated detection module by injecting the building material into a mould.

* * * * *